US00PP25227P3

(12) United States Plant Patent
Blom

(10) Patent No.: US PP25,227 P3
(45) Date of Patent: Jan. 13, 2015

(54) *CHRYSANTHEMUM* PLANT NAMED 'ZANMUSTAWHI'

(50) Latin Name: *Chrysanthemum×morifolium Ramat.*
Varietal Denomination: Zanmustawhi

(71) Applicant: Chrysanthemum Breeders Association Research B.V., Aalsmeer (NL)

(72) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 184 days.

(21) Appl. No.: 13/694,693

(22) Filed: Dec. 26, 2012

(65) Prior Publication Data
US 2014/0182025 P1 Jun. 26, 2014

(51) Int. Cl.
*A01H 5/00* (2006.01)

(52) U.S. Cl.
USPC ..... Plt./288

(58) Field of Classification Search
USPC ..... Plt./288
See application file for complete search history.

*Primary Examiner* — Anne Grunberg
(74) *Attorney, Agent, or Firm* — Steptoe & Johnson LLP

(57) ABSTRACT

A *Chrysanthemum* plant named 'Zanmustawhi' characterized by its medium sized blooms with white ray florets and a cream center and prolific branching; natural season flowering date September 24 (week 39); blooming for a period of 5 weeks.

3 Drawing Sheets

Botanical designation: *Chrysanthemum×morifolium* Ramat.

Cultivar denomination: 'Zanmustawhi'.

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmustawhi'. 'Zanmustawhi' is a product of a breeding and selection program for outdoor pot mums (garden mums) which had the objective of creating new cultivars with a double type inflorescence, a natural season flowering date around September 24 (week 39), blooming for a period of 5 weeks. 'Zanmustawhi' is a seedling resulting from a cross of the female parent id 23633 with the male parent id 46175. Plants of the new cultivar 'Zanmustawhi' differ from plants of the female parent in the following characteristics. (1) Natural season flowering date. And (2) Inflorescence size. (1) Plants of the seedling flower earlier in the season than those of the female parent. (2) Inflorescences of the seedling are larger than those of the female parent. Plants of the new cultivar 'Zanmustawhi' differ from plants of the male parent in plant vigor; plants of the seedling are less vigorous than those of the male parent.

The new and distinct cultivar was discovered and selected as a flowering plant by Wilhelmus Bemardus Blom on a cultivated field in Rijsenhout, The Netherlands in 2007. The first act of asexual production of 'Zanmustawhi' was accomplished when vegetative cuttings from the initial selection in 2007 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *Chrysanthemum* (of about 17 weeks) is shown in the accompanying drawings, the color being as nearly true as possible with color photographs of this type.

DESCRIPTION OF THE INVENTION

Figure 1:
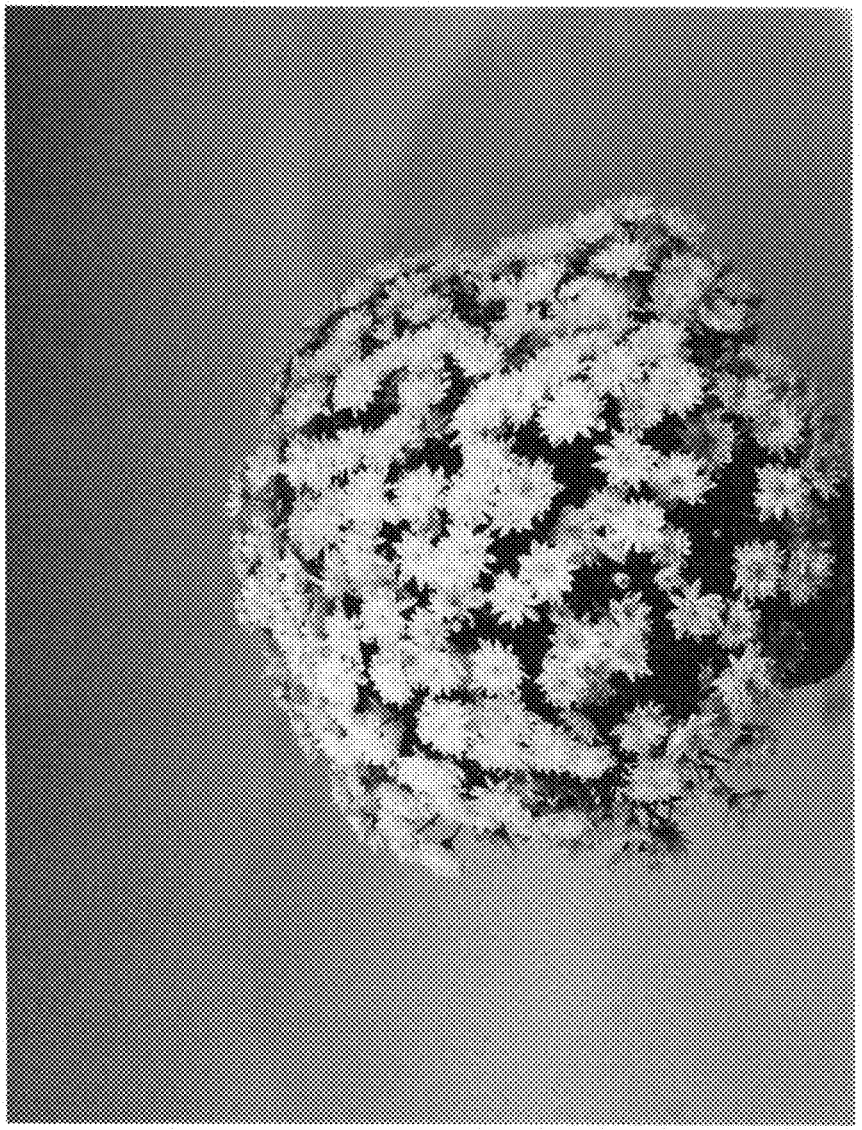
FIG. 1 shows a plant of the cultivar in full bloom.
Figure 2:
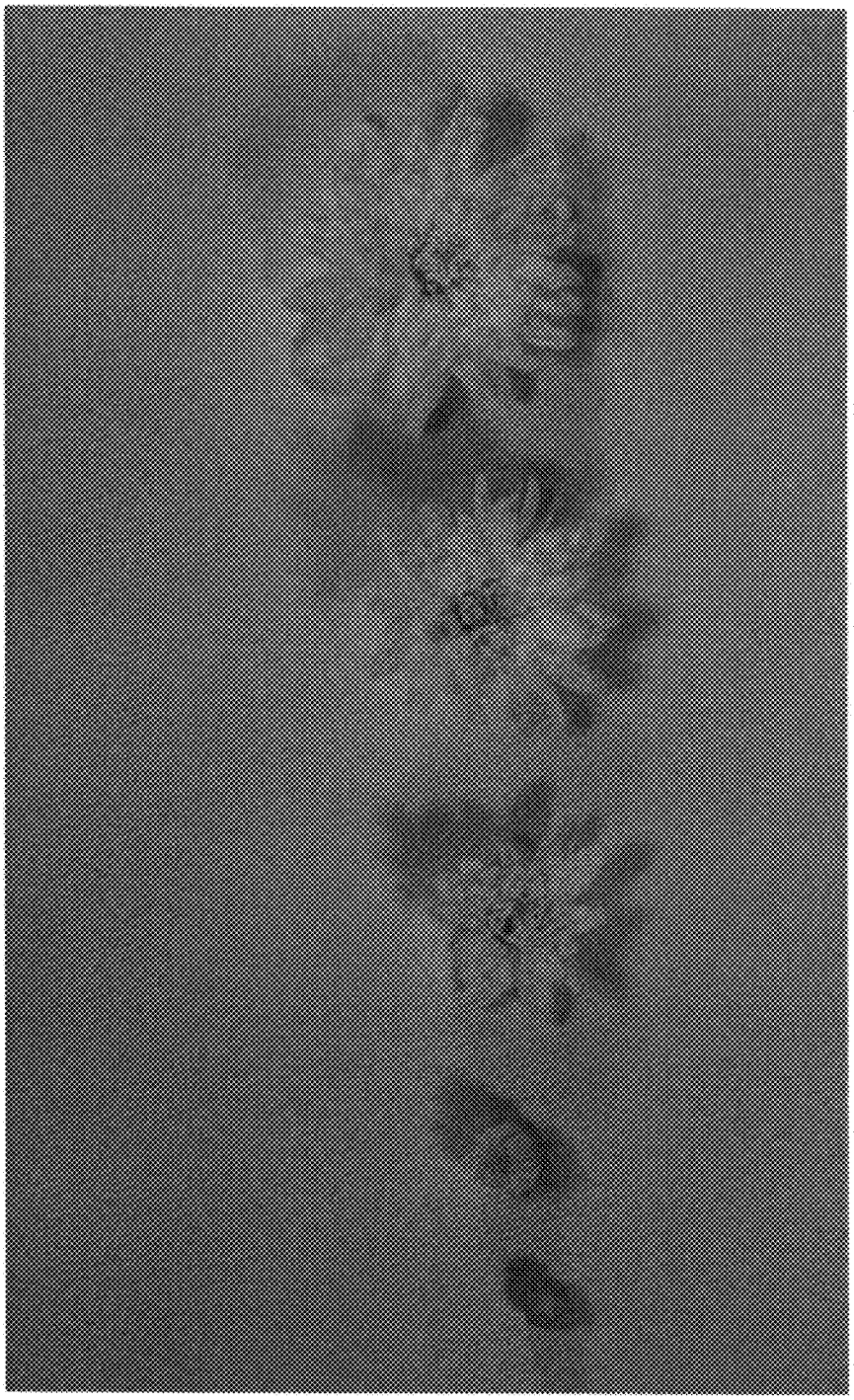
FIG. 2 shows the various stages of bloom of the new cultivar.
Figure 3:
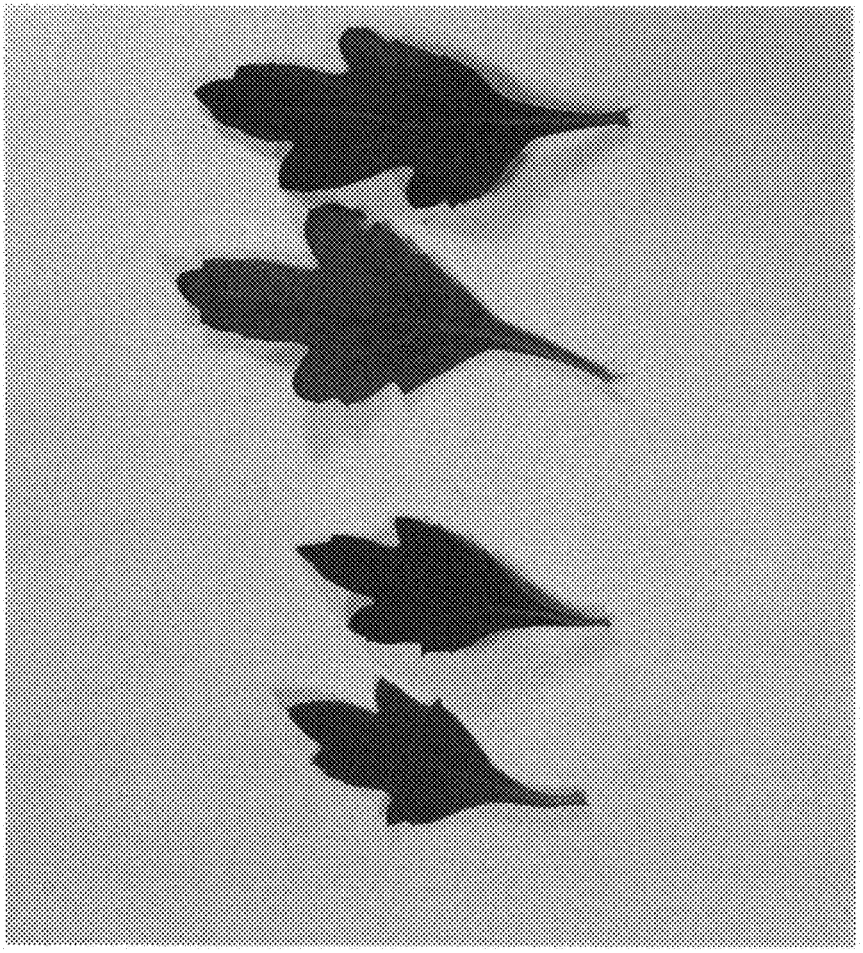
FIG. 3 shows the various stages of foliage of the new cultivar.

The observations and measurements were gathered from plants grown out door in Rijsenhout, The Netherlands under natural day length and temperature and planted in week 23 in 2012. The natural blooming date of this crop was September 24 (week 39). The average height of the plants was 2.5 cm. No growth retardants were used. No tests were done on disease or insect resistance or susceptibility. No tests were done on cold or drought tolerance. This new variety produces medium sized blooms with white ray florets with a cream center blooming for a period of 5 weeks.

From the cultivars known to inventor the most similar existing cultivar in comparison to 'Zanmustawhi' are 'Zanmudove' (U.S. Plant Pat. No. 24,618) and 'Zanmuglow' (U.S. Plant Pat. No. 22,617). When 'Zanmustawhi', 'Zamudove' and 'Zanmuglow' are being compared the following differences are noticed: (1) Inflorescence size. And (2) Natural flowering date. (1) Inflorescences of 'Zanmudove' are larger than those of 'Zanmustawhi' and 'Zanmuglow'. (2) Plants of 'Zanmustawhi' and 'Zanmudove' flower later than those of 'Zanmuglow'

The following is a description of the plant and characteristics that distinguish 'Zanmustawhi' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmustawhi'

| | |
|---|---|
| **Bud** | |
| Size: | Small; cross-section 6 mm, height 6 mm |
| Shape: | Round |
| Texture: | Pubescent |
| Outside color: | Greyed-green 191A |
| **Phyllaries** | |
| Number: | 18-20, arranged in 3 rows |
| Shape: | Elliptic |
| Apex: | Acute |
| Base: | Truncate |
| Margin: | Entire |
| Color: | Upper side: Green 137A<br>Lower side: Green 137A |
| Length and width: | 6 mm; 1 mm |
| Texture: | Pubescent |
| **Inflorescences** | |
| Type: | Double |
| Height: | 2.5 cm |
| Diameter: | 5 cm |
| Peduncle length: | 5-8 cm |
| Peduncle color: | Green 138A |
| Peduncle diameter: | 1.5 mm |
| Peduncle texture: | Pubescent |
| Number per branch: | Approx. 6 inflorescences |
| Duration of flowering: | 5 weeks |
| Seeds: | Produced in small quantities, ovate, Greyed-brown 199A, length 1.5 mm, diameter 0.5 mm |
| Fragrance: | Faint *chrysanthemum* odor |
| **Color inflorescences** | |

Center of inflorescence: Immature stage: White 155A; Mature stage: White 155D
Color of upper side of ray florets: White 155D
Color of lower side of ray florets: White 155D
Tonality from distance: A garden mum with white blooms and a cream center
Color of ray florets after aging of the plant: White 155D

| | |
|---|---|
| **Ray florets** | |
| Texture: | Upper and lower side smooth |
| Number: | 150-170 |
| Shape: | Elliptic |
| Apex: | Dentate |
| Base: | Attenuate |
| Cross-section: | Circular |
| Longitudinal axis: | Incurving to straight |
| Length of corolla tube: | 5-20 mm |
| Ray floret margin: | Entire |
| Ray floret length: | 1-2.5 cm |
| Ray floret width: | 1-3 mm |
| Ratio length/width: | Medium |
| Disc florets | Absent |
| **Receptacle** | |
| Color: | Yellow-green 145D |
| Shape: | Domed raised |
| Height: | 5 mm |
| Diameter: | 4 mm |

TABLE 1-continued

Botanical Description of *Chrysanthemum* × *morifolium* Ramat. 'Zanmustawhi'

| | |
|---|---|
| **Reproductive Organs** | |
| Androecium: | Absent |
| Pollen: | Absent |
| Gynoecium: | Present on ray florets |
| Style color: | Yellow-green 154C |
| Style length: | 4 mm |
| Stigma color: | Yellow 7A |
| Stigma width: | 1 mm |
| Ovary: | Enclosed in calyx |
| **Plant** | |
| Form: | Grown as a spray type pot mum, outdoor raised and mounded |
| Growth habit: | Spherical shape |
| Growth rate: | Medium |
| Height: | 35 cm |
| Width: | 45 cm |
| Stem color: | Greyed-brown 199A |
| Stem strength: | Strong |
| Stem brittleness: | Not brittle |
| Stem anthocyanin coloration: | Not observed |
| Internode length: | 2 cm |
| Length of lateral branch: | From top to bottom 18-20 cm |
| Lateral branch color: | Green 137 C |
| Lateral branch, attachment: | Weak |
| Lateral branch diameter: | 1.5-2 mm |
| Branching (average number of lateral branches): | Prolific with 8-10 breaks after pinching |
| Natural season blooming date: | September 24 (week 39) |
| **Foliage** | |
| Leaf color: | Upper side: Green 136B<br>Lower side: Green 138A |
| Color midvein: | Upper side: Yellow-green 147D<br>Lower side: Yellow-green 148D |
| Size: | Small; length 2-4.5 cm, width 0.8-2 cm |
| Quantity (number per lateral branches): | 24-26 |
| Shape: | Elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |
| Shape of base: | Attenuate |
| Apex: | Mucronulite |
| Petiole length: | 0.3-12 cm |
| Petiole diameter: | 1.5 mm |
| Petiole color: | Yellow-green 147D |

TABLE 2

Differences with the comparison varieties, when grown under identical conditions

| | 'Zanmustawhi' | 'Zanmudove' | 'Zanmuglow' |
|---|---|---|---|
| Inflorescence size | 5 cm | 6.5 cm | 5 cm |
| Natural season flowering date | week 39 | week 39 | week 35 |

I Claim:

1. A new and distinct *Chrysanthemum* plant named 'Zanmustawhi' as described and illustrated.

* * * * *